(12) United States Patent
Alleleyn et al.

(10) Patent No.: US 12,121,436 B2
(45) Date of Patent: Oct. 22, 2024

(54) PROSTHETIC HEART VALVE

(71) Applicant: MEDTRONIC BAKKEN RESEARCH CENTER B.V., Maastricht (NL)

(72) Inventors: Luc Alleleyn, Wittem (NL); Maurice Verbeek, Geleen (NL); Joost Ubachs, Grevenbicht (NL); Victor Duijsens, Grevenbicht (NL); Estelle Fraysse, Eindhoven (NL)

(73) Assignee: MEDTRONIC BAKKEN RESEARCH CENTER B.V., Maastricht (NL)

( * ) Notice: Subject to any disclaimer, the term of this patent is extended or adjusted under 35 U.S.C. 154(b) by 746 days.

(21) Appl. No.: 17/297,315

(22) PCT Filed: Nov. 8, 2019

(86) PCT No.: PCT/EP2019/000309
§ 371 (c)(1),
(2) Date: May 26, 2021

(87) PCT Pub. No.: WO2020/114619
PCT Pub. Date: Jun. 11, 2020

(65) Prior Publication Data
US 2022/0031452 A1 Feb. 3, 2022

(30) Foreign Application Priority Data

Dec. 4, 2018 (EP) .................................. 18210154

(51) Int. Cl.
*A61F 2/24* (2006.01)
*A61F 2/90* (2013.01)

(52) U.S. Cl.
CPC .......... *A61F 2/2418* (2013.01); *A61F 2/2427* (2013.01); *A61F 2/90* (2013.01); *A61F 2230/0069* (2013.01); *A61F 2250/001* (2013.01)

(58) Field of Classification Search
CPC ........ A61F 2/24; A61F 2/2418; A61F 2/2409; A61F 2/82; A61F 2/852; A61F 2/07;
(Continued)

(56) References Cited

U.S. PATENT DOCUMENTS 10,702,380 B2 * 7/2020 Morriss .................. A61F 2/2418
10,856,974 B2 * 12/2020 Braido .................. A61F 2/2409
(Continued)

OTHER PUBLICATIONS

International Search Report and Written Opinion issued Mar. 5, 2020 in International Appl. No. PCT/EP2019/000309.

*Primary Examiner* — Seema Mathew
(74) *Attorney, Agent, or Firm* — Medler Ferro Woodhouse & Mills PLLC

(57) ABSTRACT

A prosthetic heart valve is disclosed that is deformable between collapsed, radially uncompressed, and target conditions. The prosthetic heart valve includes an inner frame, at least one leaflet, and a braided wire mesh arranged outside and coupled to the inner frame by a coupling portion. The braided wire mesh includes a body portion between the coupling portion and a flared portion. In the radially uncompressed condition, the prosthetic heart valve forms a cavity surrounded by the braided wire mesh and the inner frame. In the target condition, only a part of the length of the body portion is radially compressed along an axis extending from an upstream side to a downstream side. In the collapsed condition, the inner frame and braided wire mesh are radially collapsed over their entire length. In the radially uncompressed condition, the body portion is tubular and the
(Continued)

Figure 1:
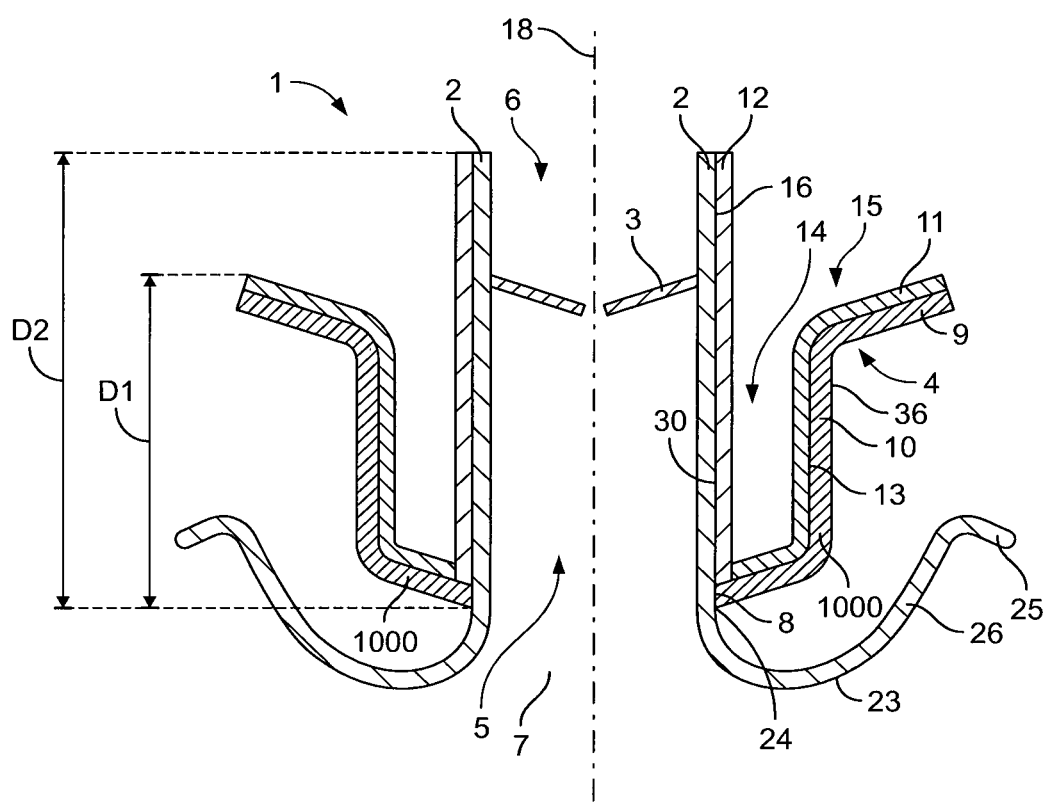

braided wire mesh has a rotationally symmetric circumference.

19 Claims, 7 Drawing Sheets

(58) Field of Classification Search
CPC ...... A61F 2220/0008; A61F 2220/0016; A61F 2/848; A61F 2002/8483; A61F 2250/0007; A61F 2220/0083
See application file for complete search history.

(56) References Cited

U.S. PATENT DOCUMENTS

| | | | |
|---|---|---|---|
| 11,298,117 B2* | 4/2022 | Hariton | A61F 2/2427 |
| 11,364,117 B2* | 6/2022 | Dale | A61F 2/2418 |
| 11,426,155 B2* | 8/2022 | Hacohen | A61F 2/2409 |
| 11,484,422 B2* | 11/2022 | Longo | A61F 2/89 |
| 11,517,436 B2* | 12/2022 | Hacohen | A61F 2/2466 |
| 11,523,900 B2* | 12/2022 | Morriss | A61F 2/2466 |
| 11,793,638 B2* | 10/2023 | Hariton | A61F 2/2409 |
| 11,844,690 B2* | 12/2023 | Jimenez | A61F 2/2418 |
| 11,872,130 B2* | 1/2024 | Hammer | A61F 2/2436 |
| 11,877,926 B2* | 1/2024 | Francis | A61F 2/2418 |
| 12,004,949 B2* | 6/2024 | Ratz | A61F 2/2418 |
| 2014/0371844 A1* | 12/2014 | Dale | A61F 2/2436 623/2.11 |
| 2015/0328001 A1* | 11/2015 | McLean | A61F 2/2427 623/2.36 |
| 2015/0351904 A1* | 12/2015 | Cooper | A61F 2/2418 623/2.1 |
| 2016/0038280 A1* | 2/2016 | Morriss | A61F 2/2436 623/2.18 |
| 2016/0095700 A1* | 4/2016 | Righini | A61F 2/2418 623/2.11 |
| 2017/0296335 A1 | 10/2017 | Thapliyal | |
| 2018/0055629 A1* | 3/2018 | Oba | A61L 27/04 |
| 2018/0177595 A1 | 6/2018 | Krans et al. | |
| 2018/0271653 A1 | 9/2018 | Vidlund et al. | |
| 2018/0296335 A1 | 10/2018 | Miyashiro | |
| 2018/0296341 A1* | 10/2018 | Noe | A61F 2/2418 |
| 2019/0038405 A1* | 2/2019 | Iamberger | B29C 39/10 |
| 2019/0183639 A1* | 6/2019 | Moore | A61F 2/2409 |
| 2019/0209304 A1* | 7/2019 | Lee | A61F 2/2475 |
| 2019/0321171 A1* | 10/2019 | Morriss | A61F 2/2436 |
| 2019/0388225 A1* | 12/2019 | Perszyk | A61F 2/848 |
| 2020/0179109 A1* | 6/2020 | Reimer | A61F 2/2418 |
| 2020/0323637 A1* | 10/2020 | Banai | A61F 2/2412 |
| 2020/0330222 A1* | 10/2020 | Miyashiro | A61F 2/2418 |
| 2022/0087814 A1* | 3/2022 | Vidlund | A61F 2/2436 |
| 2022/0265450 A1* | 8/2022 | Darekar | A61F 2/2409 |
| 2023/0125281 A1* | 4/2023 | Alleleyn | A61F 2/9525 623/1.11 |
| 2023/0200980 A1* | 6/2023 | Peterson | A61F 2/2418 623/2.17 |
| 2023/0248515 A1* | 8/2023 | Miyashiro | A61F 2/2418 623/1.14 |
| 2024/0122701 A1* | 4/2024 | Sands | A61F 2/2418 |
| 2024/0173128 A1* | 5/2024 | King | A61F 2/2418 |

* cited by examiner

PROSTHETIC HEART VALVE

The invention relates to a prosthetic heart valve.

A known prosthetic mitral valve is arranged to regulate blood flow between two chambers, the left atrium and left ventricle of a human heart. The prosthetic mitral valve comprises a stent, a cylindrical cuff, leaflets and a flange formed of braided nitinol wires. The leaflets are operable between a closed status in which the leaflets prevent the flow of blood from the left ventricle to the left atrium and an open status in which the leaflets maximally enable the flow of blood through the prosthetic valve, i.e. the leaflets restrict the flow of blood through the prosthetic valve minimally. The prosthetic mitral valve is collapsible for easy delivery and expandable in radial direction to be anchored and functioning in the heart.

The flange itself is formed of two overlaying sheets that are joined together. The flange is formed of a braided material.

The flange comprises a flared portion and a body portion and is connected to the sent at a coupling portion. On the side of the ventricle the stent protrudes into the ventricle beyond the coupling portion. On the anterior side of the prosthetic heart valve the flared portion is directly connected to the coupling portion, whereas at the posterior side the body portion is between the coupling portion and the flared portion. This means that the prosthetic heart valve has an asymmetric configuration about a central longitudinal axis because the flange forms different shapes on the anterior and posterior sides of the prosthetic heart valve. Consequently, different portions of the stent on the ventricular side are exposed. In addition, the prosthetic mitral valve has anchoring arms connected to the stent on the anterior side, whereas it has stabilizing wires connected to the flange on the posterior side for anchoring.

Preferably a prosthetic mitral valve is delivered via a catheter in a procedure sometimes referred to as transcatheter mitral valve replacement (TMVR) wherein transcatheter refers to the delivery by catheter. Transcatheter mitral valve replacement is a relatively new field. During recent developments it became clear that when delivering a valve via a catheter, it is difficult to arrange that the valve is deployed in the heart with the right orientation with respect to the anterior and posterior sides of the mitral valve annulus. In case the valve arrives in the catheter at the heart and is deployed with an incorrect orientation, it needs to be collapsed again, reoriented and expanded again or removed when this is no longer possible.

The object of the invention is to provide a prosthetic mitral valve that is suitable for delivery by catheter without risking reorientation after deploying in the heart.

According to the invention the object is reached by a prosthetic heart valve for regulating fluid flow between an upstream side and a downstream side and being deformable between a collapsed condition, a radially uncompressed condition and a target condition, comprising:

- an inner frame having a tubular shape comprising a lumen, the lumen extending from the upstream side to the downstream side in the radially uncompressed condition;
- at least one leaflet arranged within the lumen and arranged for regulation the fluid flow;
- a braided wire mesh arranged outside of the inner frame and coupled to the inner frame at a coupling portion of the braided wire mesh only, the braided wire mesh further comprising flared portion and a body portion between the coupling portion and the flared portion, wherein in the radially uncompressed condition the flared portion is positioned closer to the upstream side than the coupling portion and the body portion;

wherein in the radially uncompressed condition the prosthetic heart valve forms a cavity surrounded by the braided wire mesh and the inner frame, the cavity having an opening on the upstream side;

wherein in the target condition only a part of the length of the body portion along an axis is radially compressed, the axis extending from the upstream side to the downstream side;

wherein the collapsed condition corresponds to a condition in which the inner frame and the braided wire mesh are radially collapsed over their entire length in axial direction;

wherein in the radially uncompressed condition, the body portion being tubular; and the braided wire mesh has a rotationally symmetric circumference around the axis.

Because in the radially uncompressed condition the body portion is tubular and the braided wire mesh has a rotationally symmetric circumference around an axis extending from the upstream side to the downstream side, the orientation is not important for the implementation in a mitral valve annulus. This is because the rotational symmetry of the braided wire mesh gives the braided wire mesh the property to be able conform to the shape of the annulus irrespective of the rotational orientation of the mitral valve annulus around the axis. The body portion of the braided wire mesh being tubular gives the prosthetic heart valve the property that the braided wire mesh has the space to conform to an annulus as found at atrioventricular valves (the mitral valve and the tricuspid valve) in the human heart. Because the orientation is not important, reorientation after deploying in the heart will not be needed.

A condition in which the prosthetic heart valve is deployed and in use to regulate fluid flow, for instance as an atrioventricular heart valve of a human heart, such as a mitral valve corresponds to the target condition. Equally, the condition wherein the prosthetic heart valve is in a plastic, static model of the human heart for instance at the modelled position of the mitral valve, also corresponds to the target condition.

A braided wire mesh is a flexible structure and to flex it, it needs space. As there is a cavity surrounded by the braided wire mesh and the inner frame, the braided wire mesh is flexible in the sense that it can be compressed easily toward the inner frame and therefore the body portion can conform to the annulus of the heart between the left atrium and the left ventricle very well both in radial direction and in longitudinal direction when deforming to the target condition. In case the prosthetic heart valve would be applied at another position than in the annulus of the mitral valve, for instance to replace the tricuspid valve, the body portion can conform to the native valve structure at that position.

When implanted in a heart to replace a native valve, the conformability of the braided wire mesh makes that the braided wire mesh shape both in a cross-section perpendicular to the axis as in longitudinal direction is influenced. When implanted as an atrioventricular prosthetic heart valve, the downstream side corresponds to the ventricular side. The part of the body portion protruding into the ventricle has a larger diameter than in the annulus when implanted in the human heart to replace the native mitral valve.

When replacing the native mitral valve, in case the prosthetic heart valve is pushed in the direction of the atrium by the blood pressure in the left ventricle being higher than the blood pressure upstream in the left atrium, the diameter of the body portion of the braided wire mesh in the left ventricle even increases. This is because the body portion can conform easily when compressed;
the body portion is exposed to friction in the annulus;
the braided wire mesh is connected to the inner frame at the coupling portion only;
the body portion is between the coupling portion and the flared portion and in the radially uncompressed condition the flared portion is positioned closer to the upstream side than the coupling portion and the body portion.

As the body portion between where it is exposed to friction and the coupling portion is compressed in longitudinal direction due to the prosthetic heart valve being pushed in the direction of the atrium, the radial dimension of the braided wire mesh in the left ventricle increases.

The similar situation applies when implanted to replace the native tricuspid valve. Therefore, the conformity is also advantageous to anchor the prosthetic heart valve.

The cavity surrounded by the braided wire mesh and the inner frame is an aspect that provides flexibility as the body portion can be pushed in the direction of the inner frame without becoming less deformable by being in contact with the inner frame. Apart from a contact to another structure, such as an inner frame decreasing deformability irrespective of the properties of the other structure, an inner frame preferably provides a lumen with a stable, tubular shape to arrange optimal closure of the lumen by the at least one leaflet in the closed state. Contact of the body portion with the inner frame would therefore even more decrease the flexibility of the body portion.

The cavity therefore allows that the braided wire mesh flange can be more flexible, and the inner frame can provide more stability to the shape of the lumen than without the cavity.

Moreover, as the braided wire mesh also comprises a flared portion that is closer to the upstream side than the coupling portion in the radially uncompressed condition, in a target condition in the heart as an atrioventricular valve, the flared portion is on the atrial side. As the flared portion is flared, it obviously has a larger diameter than the body portion, it provides anchoring to keep the prosthetic heart valve from being pushed into the ventricle, i.e. the left ventricle in case the prosthetic heart valve is implanted to replace a mitral valve.

As the body portion provides anchoring to keep the prosthetic heart valve from being pushed into the atrium and the flared portion is on the atrial side where it provides anchoring to keep the prosthetic heart valve from being pushed into the ventricle, the prosthetic heart valve is arranged to provide anchoring in both directions.

Another advantageous aspect of the braided wire mesh being connected to the inner frame at a coupling portion only is that the prosthetic heart valve can be compressed to occupy a low volume in the collapsed condition. Without a further connection to the inner frame, there is no need for the braided wire mesh be folded back after first flaring out at the flared portion to reach the inner frame and make the connection. Advantageously the prosthetic heart valve according to the invention does not need to comprise additional material which obviously would consume additional volume. In the collapsed condition, the volume of the braided wire mesh is preferably as small as possible to increase maneuverability and deliverability. Moreover, folding the braided wire mesh back to make another connection to the inner frame would necessarily increase the diameter of the prosthetic heart valve in collapsed condition as two layers of the braided wire mesh will need to be accommodated in the radial direction. Without being connected to the inner frame at the coupling portion, the diameter of the prosthetic heart valve in collapsed condition is kept minimal according to the invention. The mitral valve annulus is relatively large. Both in case the prosthetic heart valve is delivered as a mitral valve by catheter via a transseptal approach or via a transapical approach profit from a small diameter in collapsed condition as the catheter diameter can be kept small.

In a further embodiment of the prosthetic heart valve, in the rotationally uncompressed condition the inner frame is rotationally symmetric around the axis at least at the coupling portion.

Apart from deforming and thereby absorbing forces, the braided wire mesh transfers a part of the radial compression forces of the target condition to the coupling portion and on to the inner frame. Having rotational symmetry around the axis at the coupling portion of the braided wire mesh, the inner frame also has a rotational symmetric circumference. As the inner frame and the braided wire mesh have a symmetric circumference around the same axis, which means that they are concentric, the radial forces are transferred to the inner frame in a way that has low dependency on the angular orientation around the axis.

As the inner frame is rotationally symmetric it reacts to transferred radial compression forces in a way that has low dependency on the angular orientation around the axis.

This further contributes to reducing the need for reorientation.

In a further embodiment of the invention the prosthetic heart valve is provided with a lumen wall comprising the inner frame, the lumen wall being arranged to restrict the flow of blood through the lumen wall; and a flange which comprises means to restrict flow of blood through mazes of the braided wire mesh and comprises the braided wire mesh forming a skeleton of the flange.

As the lumen wall is arranged to restrict the flow of blood through the lumen wall and the flange comprises means to restrict flow of blood through mazes of the braided wire mesh, leakage of blood between the upstream side and the downstream side parallel to the one or more leaflets is restricted which provides for an improved functionality of the prosthetic heart valve.

Where the flared part comprises means to restrict flow of blood through the mazes, the flared part contributes to restrict paravalvular leakage, i.e. leakage of blood between the prosthetic heart valve and the tissue of the heart, as it conforms well.

In a further embodiment of the invention the prosthetic heart valve is provided with means to restrict flow of blood through the mazes of the braided wire mesh is formed by a layer of elastic material attached to the braided wire mesh.

Because the material is attached to the braided wire mesh, it follows the shape of the braided wire mesh. As the braided wire mesh conforms the shape of the heart, which is dynamic and therefore dynamically changes shape, the exterior surface area of the flange dynamically changes. Because the means comprise an elastic material, the means are arranged to follow the dynamic changes of the flange.

The elastic properties are advantageous as well to accommodate the collapsed condition of the prosthetic heart valve in which the braided wire mesh elongates.

In a further embodiment of the invention the prosthetic heart valve is provided with a lumen wall comprising a further layer of elastic material.

The elastic properties of the material are advantageous to accommodate the inner frame to extend in axial direction when being collapsed. This allows for the prosthetic heart valve to have a small diameter in collapsed condition. A small diameter is advantageous to be able deliver the prosthetic heart valve using a catheter. A small diameter for instance is advantageous for transseptal delivery by catheter as the smaller the diameter, the smaller the puncture between right atrium and left atrium can be. Below a threshold puncture size, the puncture does not have to be closed at the end of the delivery procedure by sutures which both makes the delivery procedure faster and reduces a risk by eliminating a step.

In yet another embodiment of the invention the prosthetic heart valve is provided with a braided wire mesh comprising a mesh surface that at the body portion faces the inner frame, the braided wire mesh surface being lined with the means to restrict flow of blood through the mazes, the means being formed by a liner with low permeability for blood, and the inner frame comprising an inner frame surface facing the cavity, the outer surface being lined with the further layer of material formed by a further liner with low permeability for blood.

As the mesh surface of the braided wire mesh and the outer surface of the inner frame face each other, the liner with low permeability for blood and the further liner with low permeability for blood face each other and can be attached to each other at the coupling portion to provide optimal leakage restriction. In an advantageous embodiment, the layer of elastic material and the further layer of elastic material are formed by 2 parts of one sheet. This provides optimal leakage restriction as well as easy production as attaching only one sheet suffices to complete production.

In another embodiment of the invention, the prosthetic heart valve includes a braided wire mesh forming a plurality of mazes with four corners; the mazes each having a first diagonal and a second diagonal, in the radially uncompressed condition the first diagonal having a larger perpendicular projection in a plane comprising the axis than in a plane perpendicular to the axis and the second diagonal having a larger perpendicular projection in a plane perpendicular to the axis than in a plane comprising the axis; and the first diagonal has a smaller dimension than the second dimension in the body portion in the radially uncompressed condition.

Because the first diagonal, which mainly extends along the plane comprising the axis has a smaller dimension than the second diagonal, which mainly extends in the plane perpendicular to the axis, the four-cornered mazes can extend more in axial direction than in the tangential direction. The extensibility in axial direction is advantageous to obtain a small diameter in collapsed condition.

In a further embodiment of the invention the prosthetic heart valve includes a the braided wire mesh forming a plurality of mazes each comprising four corners and four edges, wherein at least 3 corners form a corner of more than one maze; the at least 3 corners are formed by crossings of a plurality of wire sections; and the wire sections being arranged to slide with respect to each other at the crossings.

Because the wire sections can slide with respect to each other at the crossings, the dimensions of the edges, i.e. the parts of the wire sections between two consecutive corners, can change under application of radial compression and angles between the wire sections at the corners can change easily. As the corners of the mazes where the wire sections can slide over each other are corners to at least 3 mazes, sliding wire sections will reposition a corner of those at least 3 mazes. The effect of this is that the mazes can easily adapt under radial compression.

Where the maze comprises a corner that is not formed by a crossing, such a corner is a corner of a single maze only.

In a further embodiment of the invention the prosthetic heart valve includes a braided wire mesh having a first dimension along the axis; the inner frame has a second dimension along the axis; and the second dimension is at least as large as the first dimension in the radially uncompressed condition; and the first dimension is larger than the second dimension in the target condition under influence of elongation of the body portion of the braided wire mesh under radial compression of the part of the body portion.

As indicated earlier in the target condition only a part of the body portion is radially compressed. The combination of the second dimension being at least as large in the radially uncompressed condition and the first dimension being larger in the target condition because of elongation of the body portion due to radial compression of the part of the body portion means that a minimal amount of material is used to form the braided wire mesh and the inner frame to fit into the annulus where radial compression will be present as well. Using a minimal amount of material contributes to obtaining a small volume in compressed condition which is beneficial for delivery by catheter.

As the first dimension is larger than the second dimension in the target condition, when implanted as a prosthetic mitral valve and being in a target condition, the prosthetic heart valve is arranged such that the flared portion protrudes further into the atrium in axial (i.e. longitudinal) direction than the inner frame.

By protruding further into the atrium, there is a larger surface of the flared portion that can contribute to receive axial forces of the heart wall between left atrium and left ventricle. This contributes to anchoring of the prosthetic heart valve.

In case the flared portion comprises means to restrict flow of blood through the mazes, it is advantageous that the flange can protrude into the atrium further to provide for optimal sealing of the annulus, especially as the annulus has a non-circular shape (which approximates a D-shape in a top view and a saddle shape in a side view) and even changes shape dynamically because of the heart contractions. Therefore, the inner frame can be optimized for stability and the flange can be optimized for sealing.

In a further embodiment of the invention the prosthetic heart valve includes a braided wire mesh formed by one single continuous wire.

Because the braided wire mesh is formed by a single continuous wire, the braided wire mesh has a rotationally symmetric circumference around the axis.

In a further embodiment of the invention a prosthetic heart valve is provided, comprising a plurality of hooks attached on the downstream side and pointing away from the lumen and towards the upstream side in the radially uncompressed state; wherein the hooks are arranged to capture native leaflets in deployed condition, the hooks being distributed at rotationally symmetric positions around the axis.

As the hooks capture the native leaflets, the native leaflets are prevented from causing uncontrolled flow patterns or restriction of the flow in the heart. The hooks are distributed at rotationally symmetric positions around the axis.

In an advantageous further embodiment, the hooks are attached to the inner frame.

As the braided wire mesh is arranged to conform to the heart easily, the inner frame is shielded from deformation in use. By being attached to the inner frame, the hooks therefore are shielded from being moved by contractions of the heart via forces exerted via the braided wire mesh to the prosthetic heart valve.

In a further embodiment of the invention a prosthetic heart valve is provided, wherein the hooks are attached to the inner frame at an attachment end and of the hooks and comprise a top at an opposite side of the hooks and comprise a hook body between the attachment end and the top, the hooks having a surface that at the hook body at least partially faces the braided wire mesh in radially uncompressed condition, wherein the hooks are curved and the surface at the top at least partially faces the upstream side or radially outward.

As the surface that at least partially faces the braided wire mesh in radially uncompressed condition at the top at least partially faces the upstream side or radially outward, the top is arranged not to pierce into tissue of the heart. Still the hooks provide anchoring of the prosthetic heart valve. Without piercing into tissue of the heart, the heart will be less irritated (i.e. the situation is more atraumatic). Piercing in the tissue of the heart is also detrimental to the conforming properties of the flange as the heart dynamically changes shape under contraction. Where the hooks pierce in the heart wall, the contraction forces would be transferred by the hooks to the inner frame whereas the conformability to the contraction is provided by the braided wire mesh and not the inner frame.

In a further embodiment of the invention, the prosthetic heart valve is provided with a hook body comprising at least one leg having a center line extending between the attachment end and the top and wherein a dimension of the at least one leg perpendicular to the center line tapers at the top.

As the leg is tapered, the curvature can vary more easily thereby improving the conformity of the hooks to the heart.

In a further embodiment of the invention, the prosthetic heart valve is provided with a hook body comprising at least one leg and having a center line extending between the attachment end and the top and a dimension of the at least one leg perpendicular to the center line tapers at the attachment end.

As the leg is tapered, the orientation of the legs in the target condition can vary more easily thereby improving the conformity of the hooks to the heart when implanted for instance as a prosthetic mitral valve.

In a further embodiment of the invention, a prosthetic heart valve includes a braided wire mesh forming a skeleton of a flange and the flange comprises a single layer of the braided wire mesh.

Comprising a single layer of the braided wire mesh instead of two joined layers such as in a known prosthetic mitral valve has the advantage that the flange can more easily conform to the shape of the annulus when implanted in a heart. In addition, the prosthetic heart valve according to this embodiment has the advantage that it can be compressed to a smaller radius than in case it would have had two joined layers, as each layer obviously occupies space.

Various embodiments of the invention will now be described by way of example only with reference to schematic figures. Where equal numbers are used in the figures, similar features are referred to.

Figure 2:
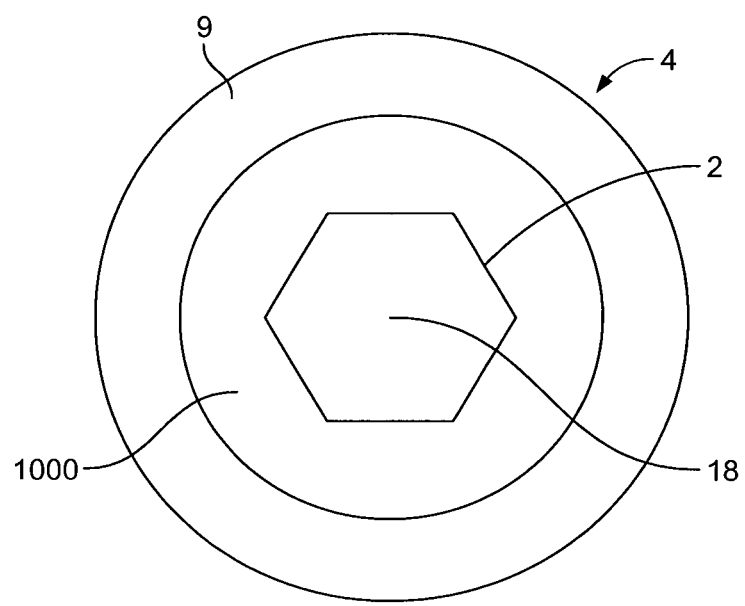
Figure 3:
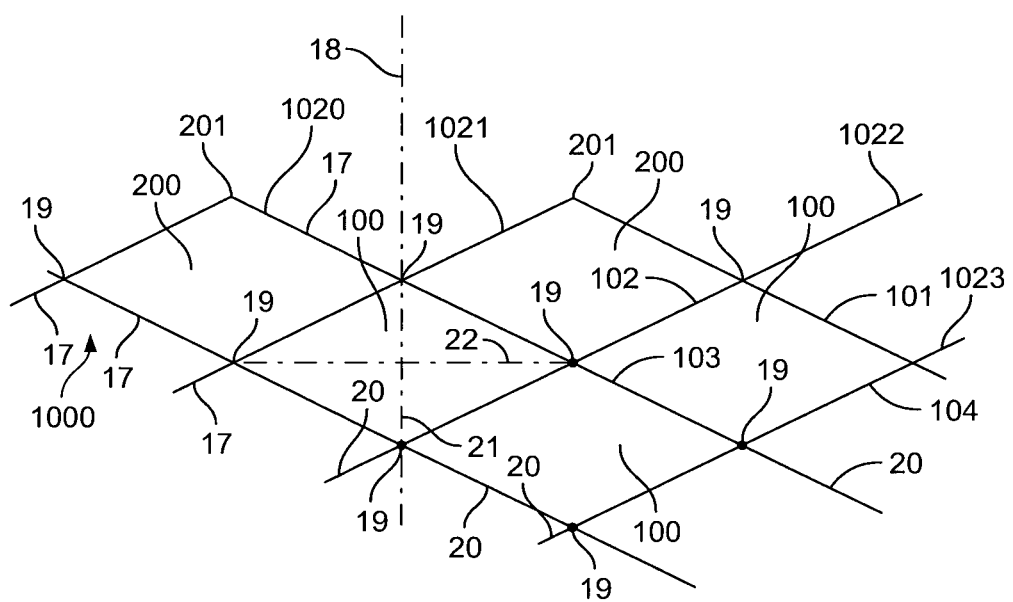
Figure 4:
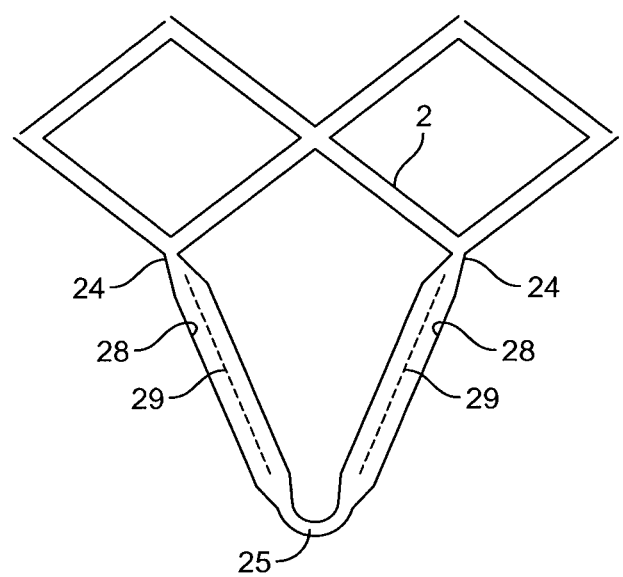
Figure 5:
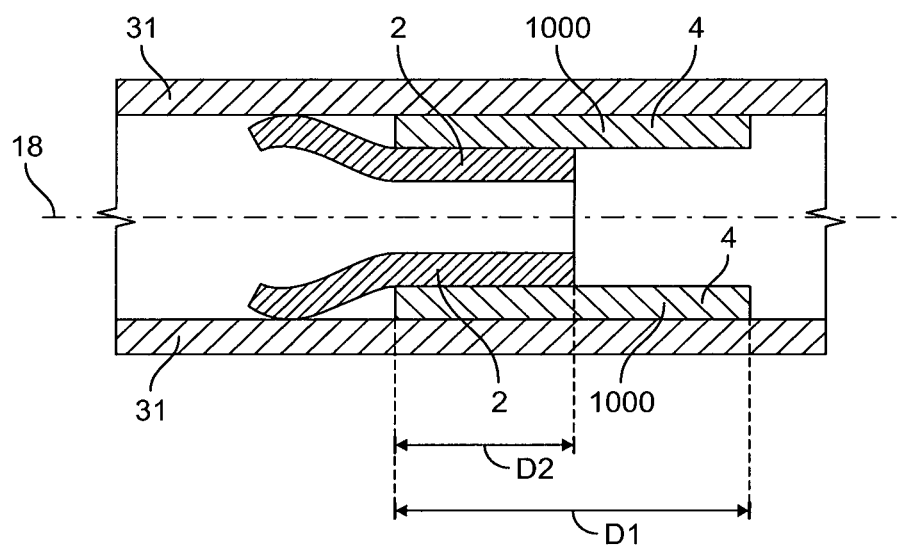
Figure 6:
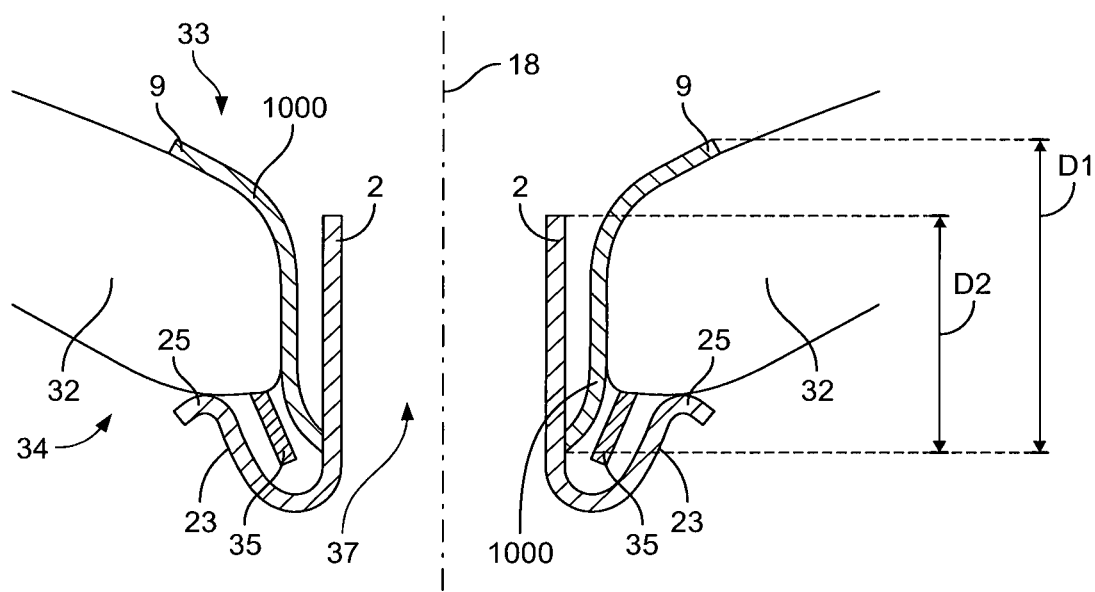
Figure 7:
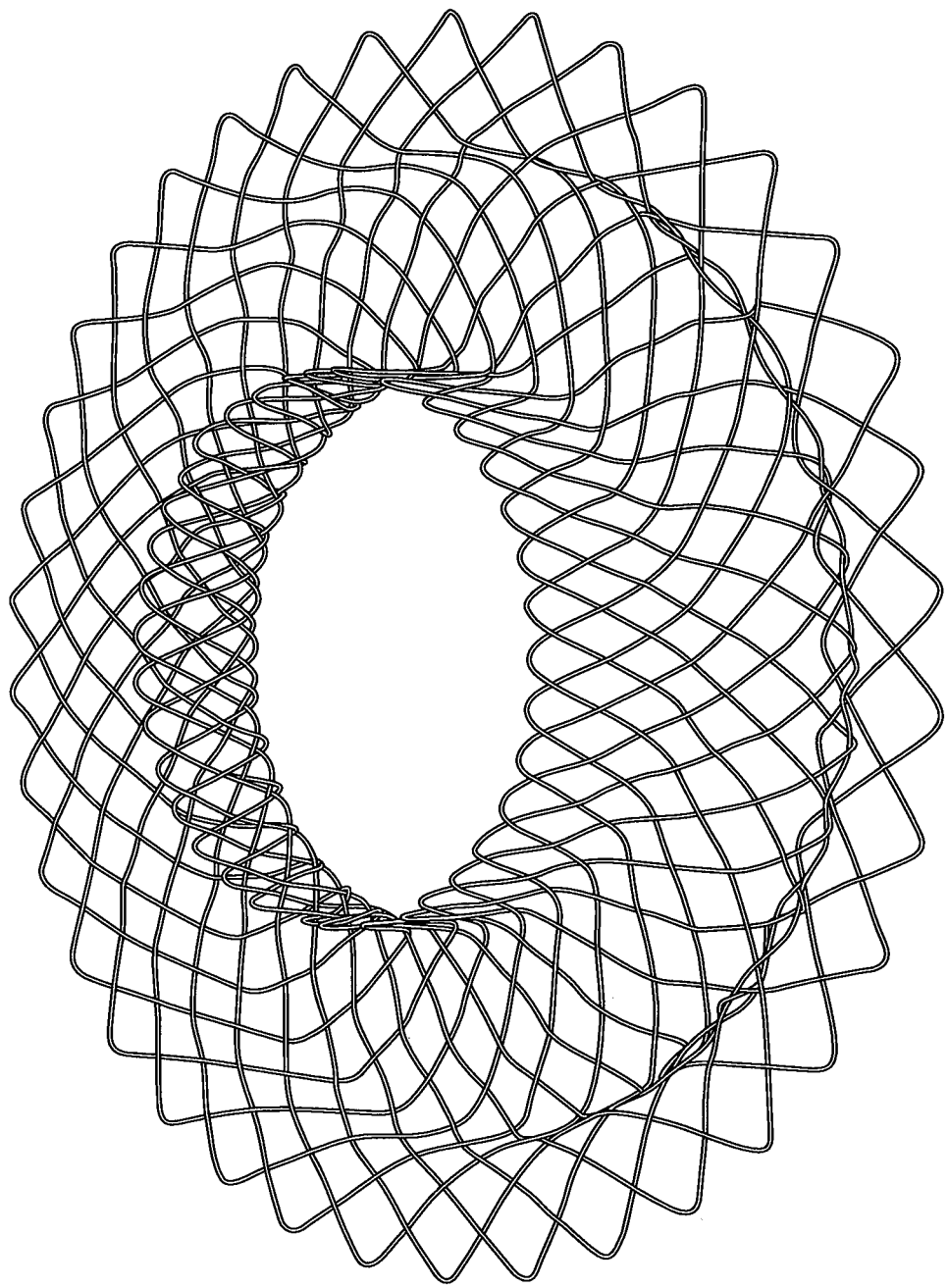

FIG. 1 depicts a cross section of an embodiment in radially uncompressed condition FIG. 2 depicts a view from the upstream side to the downstream side of an embodiment in radially uncompressed condition FIG. 3 depicts mazes of the braided wire mesh of the flange of an embodiment of the invention FIG. 4 depicts tapered parts of a hook of an embodiment of the invention FIG. 5 depicts a prosthetic heart valve according to the invention in collapsed condition in a capsule of a catheter FIG. 6 depicts a prosthetic heart valve according to the invention in a target condition FIG. 7 depicts a prosthetic heart valve according to another embodiment of the invention in a radially uncompressed condition.

Herein, a low permeability for blood corresponds to not being permeable for blood below a blood pressure below a threshold pressure. For a mitral valve the threshold pressure is 90 mm Hg, for a tricuspid valve, the threshold pressure is 15 mm Hg.

Radially Uncompressed Condition

In an embodiment of the invention a prosthetic heart valve (1) comprises an inner frame (2), two leaflets (3) and a braided wire mesh (1000).

This is shown in FIG. 1 which depicts the prosthetic heart valve in radially uncompressed condition. In this embodiment the prosthetic heart valve is a prosthetic mitral valve suitable transcatheter mitral valve replacement (TMVR). Moreover, it is suitable for transseptal delivery.

The inner frame (2) is made by laser cutting mazes in metal tube. The metal is a pseudoelastic metal, in this case nitinol, a nickel titanium metal alloy.

The inner frame (2) has a tubular shape comprising a lumen (5) that extends from an upstream side (6) to a downstream side (7) of the prosthetic heart valve.

Upstream (6) side and downstream side (7) are used here even if the prosthetic heart valve is not implanted or even near a fluid as the prosthetic heart valve is arranged to regulate fluid flow between the upstream (6) side and downstream side (7).

The radially uncompressed condition corresponds to a condition in which the prosthetic heart valve is placed on a horizontal surface with its downstream side (7) or its upstream side (6).

The braided wire mesh (1000) is arranged outside the inner frame (2). The braided wire mesh forms a skeleton of a flange (4). The flange (4) comprises a single layer of a braided wire mesh (1000) that is coupled to the inner frame (2) at a coupling portion (8) of the flange. The braided wire mesh (and since that forms the skeleton of the flange (4) therefore the flange (4) also) further comprises a flared portion (9) and a body portion (10). The body portion (10) forms the connection between the flared portion (9) and the coupling portion (8). In the radially uncompressed condition the flared portion (9) is closest of the 3 portions (i.e. the coupling portion, the body portion and the flared portion) to the upstream side (6) and the coupling portion is closest of the 3 portions to the downstream side (7).

The flange (4) further comprises a layer (11) of elastic material that is attached to the braided wire mesh (1000) by stitches (stitches not shown). The elastic material is a polyurethane fabric. The braided wire mesh (1000) comprises a braided wire mesh surface (13) that at the body portion (10) faces the inner frame (2). The layer (11) of elastic material is attached to the braided wire mesh surface (13).

The prosthetic heart valve (1) forms a cavity (14) that is surrounded by the braided wire mesh (1000) (and the flange (4)) and the inner frame (2). The inner frame (2) comprises an inner frame surface (16) that faces the cavity (14). The cavity (14) is not completely surrounded and has an opening (15) on the upstream side (6).

The lumen (5) is enclosed by a lumen wall (30). The lumen wall (30) comprises the inner frame (2) and a further layer (12) of elastic material. The elastic material is a polyurethane fabric. The further layer (12) of elastic material is attached to the outer surface (16) by stitches (stitches not shown).

The layer (11) of elastic material and the further layer (12) of elastic material are made from extensible fabric that has a low permeability for blood.

The layer (11) of elastic material therefore forms a liner with low permeability for blood and the further layer (12) of elastic material therefore forms a further liner with low permeability for blood.

The permeability is chosen such that the material is not permeable below a blood pressure of at least 90 mm Hg which pressure corresponds to the pressure required to open the aortic valve.

At the coupling portion (8) the layer (11) of elastic material and the further layer (12) of elastic material are connected to each other by stitches to form a blood tight seam. The blood tight seam functions as a seal.

The leaflets (3) are arranged in the lumen (5) and is arranged to regulate the fluid flow. The leaflets (3) are of bovine pericardial tissue.

As the inner frame (2) and the flange (4) are lined with the layer (11) of elastic material and the further layer (12) of elastic material, fluids can only pass through the prosthetic heart valve (1) through the lumen and thus the leaflet assembly (3).

The inner frame (2) is made by laser cutting mazes in a metal tube such that the shape of the inner frame (2) in the radially uncompressed condition is constant along the axial direction although there may be some end effects at the ends that after incorporating into the prosthetic valve (1) are on the downstream side (7) and the upstream side (6).

The inner frame (2) and the flange (4) each have a rotationally symmetric circumference around an axis (18) extending from the upstream side (6) to the downstream side (7). This is shown in FIG. 2. Moreover, the inner frame (2) is rotationally symmetric around the axis (18).

Having a rotationally symmetric circumference around the same axis, means that the inner frame (2) and the flange (4) are concentric.

The braided wire mesh (1000) is formed by a single continuous wire (17) which in this embodiment is made from a pseudoelastic metal, in this case nitinol. This is shown in FIG. 3. The wire from which the braided wire mesh (1000) is formed has a circular cross section. The diameter of the wire in that cross section is 0.25 mm.

A braided wire mesh (1000) is a wire mesh wherein at least 3 different sections of wire are interlaced. In FIG. 3 a first section (1020) of wire is shown to be interlaced with a second section (1021) of wire, a third section (1022) of wire. The first section (1020) crosses the second section (1021) on the exterior side of the braided wire mesh (1000), i.e. the side facing away from the inner frame (2) and crosses the third section (1022) on the interior side of the braided wire mesh, i.e. the side facing the inner frame (2). This structure repeats and for instance at a next crossing the first section (1021) would cross a fourth section (1023) on the exterior side again.

The braided wire mesh (1000) is braided such that a plurality of mazes (100,200) is formed that each has 4 corners that when considered with respect to each other far a single maze can be referred to as a northern corner, a western corner, a southern corner and an eastern corner. Herein, the mazes (100) are viewed from the exterior side towards to the axis (18) with the axis running from north to south. The skilled person will appreciate that the orientation in the names refers to a single maze as the southern corner of a first maze may form the norther corner of another maze.

In a similar view, all mazes have a northeastern edge (101), a northwestern edge (102), a southwestern edge (103) and a southeastern edge (104) when referring to a single maze. Each edge is formed by a part of a wire section (20).

Although the wire (17) in this example is a continuous wire, the wire can be seen to be composed out of separate continuous wire sections (20) each extending from the downstream side (7) of the prosthetic heart valve (1) to the upstream side (6) of the prosthetic heart valve.

Except for a row of end mazes at the upstream end of the braided wire mesh and a row of end mazes at the downstream end of the braided wire mesh (1000), the 4 corners of each maze (100) are each formed a crossing (19), i.e. a southern crossing at the southern corner, a northern crossing at the northern corner, a western crossing at the western corner and an eastern crossing at the eastern corner.

For mazes (100) with those 4 crossings, the south western edge (103) runs between the southern crossing (19) and the western crossing (19).

Each crossing (19) forms a corner of 3 or 4 mazes (100,200).

In addition to the mazes (100) wherein each of the four corners is formed by a wire crossing, the braided wire mesh (1000) comprises plurality of end mazes (200), which form the last row of mazes of the braided wire mesh where it is attached to the inner frame (2) and the last row of mazes at the flared portion (9). The end mazes (200) also have 4 corners, but one of the corners is not formed by a crossing but a bend (201) of the wire (17) where two wire sections (20) connect to each other. This corner is a corner of that end maze (200) only, not of other mazes. The other 3 corners of the end mazes (200) however, are corners of 3 or 4 mazes (100,200).

Herein the mazes (100) wherein each corner is formed by a crossing (19) will also be referred to as an intermediate maze.

In the braided wire mesh a wire section (20) forms the same type of edge all the way through the wire section for intermediate mazes, i.e. for every maze (100) where the 4 corners are formed by 4 crossings (19) along which it runs. As one of the corners of the end mazes (200) is not formed by a crossing, this does not hold for these mazes. Thus, for the mazes (100) where the 4 corners are formed by 4 crossings, i.e. for intermediate mazes (100), if a part of a wire section forms a southwestern edge (103) of a maze, the parts of the same wire section forming edges of other mazes also form southwestern edges.

In the radially uncompressed condition that is currently described, the edges (101,102,103,104) of the mazes (100, 200) have dimensions of about 1.7 to 3.0 mm and the dimensions vary with the position in the braided wire mesh (1000).

At the crossings (19) of the plurality of mazes (100) the wire sections (20) are not connected to each other, not twisted around itself but a wire section (20) either crosses another wire section (20) on the exterior side or the interior side of the braided wire mesh (1000). This has the advantage that the wire sections (20) can slide over each other. This means that the edges of a maze (100, 200) do not necessarily have to maintain the same length under different radial compression conditions. This makes the braided wire mesh (1000) conforms easily when radial pressure is applied while at the same time extending in axial direction under application of such pressure.

The mazes (100) wherein the four corners are formed by crossings (19) as well as the end mazes (200) each comprise a first diagonal (21) and a second diagonal (22). The first diagonal (21) runs from the northern corner to the southern corner of the corresponding maze. The second diagonal (22) runs from the western corner to the eastern corner of the corresponding maze.

At the body portion (10) the first diagonal (21) is smaller than the second diagonal (22). As the wire sections (20) are not connected at the crossings (19), the relative dimensions of the first diagonal (21) and the second diagonal (22) can be changed under the influence of radial compression.

Under radial compression the dimension of the second diagonal (22) decreases which already changes the ratio. However, as the wire (17) keeps its length, a smaller second diagonal (22) means that the first diagonal (21) of at least some mazes (100, 200) must increase, which further changes the ratio.

The skilled man will appreciate that even if the wire sections would have been connected at the crossings (19), the relative dimensions of the first diagonal (21) and the second diagonal (2)) can be changed under the influence of radial compression when deforming the angles between the wire sections (20) at the crossings (19).

Although in FIG. 3 the wire sections (20) are shown to be straight, this is for the purpose of explaining the invention and in many mazes (100,200) the wire sections (20) are curved.

The prosthetic heart valve (1) further comprises a plurality of hooks (23) attached to the inner frame (2) on the downstream side (7). This is shown in FIG. 1. The hooks (23) point away from the lumen (5) and towards the upstream side (6). The hooks (23) are arranged to capture native leaflets (35) when deployed in a mitral valve annulus of a human heart. This is shown in FIG. 6. The hooks (23) are distributed at rotationally symmetric positions around the axis (18).

The hooks (23) each comprise an attachment end (24) where they are attached to the inner frame (2). In this embodiment the hooks (23) are formed together with the inner frame (2), however, they may be produced separately and attached to the inner frame (2) later in other embodiments.

The hooks (23) further each comprise a top (25) at side of the hooks opposite to the attachment end (24).

The hooks (23) further each comprise a hook body (24) which has an elongated shape.

The hooks (23) comprise a surface (27) that at the hook body (24) partially faces the flange (4). The hooks (23) are curved and the surface of the top (25) partially faces the upstream side (6) and partially faces radially outward.

The hooks (23) in this embodiment each comprise two legs (28). This is shown in FIG. 4 which depicts a frontal view in the direction of the axis (18) where the hook (23) has been depicted as it is was made flat for the purpose of explanation, i.e. in the drawing the hook does not point away from the lumen (5) but the legs are parallel to the lumen (5). In FIG. 4 the hook (23) is attached to two bottom corners of different mazes of the inner frame (2).

The legs have a center line (29) that extends between the attachment end (24) and the top (25). The dimension of the hook legs (28) perpendicular to the center line (29) tapers towards the top at the top (25).

Similarly, the dimension of the hook legs (28) perpendicular to the center line (29) tapers at the attachment end (24) by becoming smaller towards the attachment end (24).

The flange has a first dimension (D1) along the axis (18). The inner frame (2) has a second dimension (D2) along the axis (18). The second dimension (D2) is larger than the first dimension (D1) in this radially uncompressed condition.

Collapsed Condition

The same embodiment will now be described in a collapsed condition. This will be done with reference to FIG. 5. In this figure the prosthetic heart valve (1) is depicted in a capsule of a catheter. In FIG. 5 the layer (11) of elastic material and the further layer (12) of elastic material are not shown for clarity reasons.

The capsule has a cylindrical capsule wall (31). In this embodiment the collapsed condition is not a stable condition and can be maintained only as long as the prosthetic heart valve (1) stays inserted in the capsule and is exposed to radial pressure by the capsule wall (31).

The inner frame (2) is radially collapsed over the entire length in the axial direction of the inner frame (2).

The braided wire mesh (1000) and thereby the flange (4) is also radially collapsed over the entire length in the axial direction of the braided wire mesh (1000).

From the collapsed condition the prosthetic heart valve (1) can return to the radially uncompressed condition and the target condition without any permanent deformations in this embodiment because the inner frame (2) and the braided wire mesh (1000) are made of nitinol which has pseudoelastic properties. As the flange (4) comprises a layer (11) of elastic material to restrict the flow of blood through the mazes (100,200) and the lumen wall (30) comprises a further layer (12) elastic material, these layers are arranged to return to the radially uncompressed and target condition elastically as well.

In this case the hooks (23) are folded back and extend both away from the inner frame (2) and the flange (4).

In this collapsed state, the first dimension (D1) is larger than the second dimension (D2). This is the result of the braided wire mesh (1000) being totally collapsed in the capsule of the delivery catheter (tool).

Target Condition

The same embodiment will now be described in a target condition. This will be done with reference to FIG. 6. In this figure the prosthetic heart valve (1) is depicted as deployed in the annulus (37) of a mitral valve in a human heart. The annulus (37) is an opening in the heart wall (32) separating the left atrium (33) and the left ventricle (34) of the human heart.

In FIG. 6 the layer (11) of elastic material and the further layer (12) of elastic material are not shown for clarity reasons.

The target condition is a condition wherein only a part of the length of the body portion (10) along the axis (18) is radially compressed.

A condition in which the prosthetic heart valve (1) is deployed and in use to regulate fluid flow, for instance as a mitral valve in a human heart corresponds to the target condition.

The heart wall (32) exerts radial pressure to the braided wire mesh (1000) of the flange (4) at the annulus (37). This pressure is not symmetrically applied and the shape of the heart wall (32) in the atrium is not constant around the axis (18). Therefore, the flared portion (9) reaches into the left atrium (33) differently around the axis (18).

Between the hooks (23) and the braided wire mesh (1000) two native leaflets (35) are captured. Even though the exerted radial pressure is asymmetric, the resulting radial compression of the braided wire mesh (1000) and thereby of the flange (4) causes the body portion (10) of the braided wire mesh (1000) to elongate in axial direction such that the first dimension (D1) increases.

The first dimension (D1) is larger than the second dimension (D2) in this target condition. In addition, the tops (25) of the hooks (23) are positioned against the heart wall (32). As the prosthetic heart valve (1) in radially uncompressed condition has the flared portion (9) closer to the hooks (23), the flared portion (9) exerts a force that pushes the top (25) of the hooks against the heart wall (32) which helps anchor the prosthetic heart valve (1).

The above embodiment should be regarded as illustrative rather than restrictive, and it should be appreciated that variations may be made by a person skilled in the art without departing from the scope of the present invention.

For instance, the layer (11) of elastic material or the further layer (12) of elastic material may, instead of being stitched, be glued to the flange (4) and inner frame (2) respectively in other embodiments or by be placed on a flange surface (36) facing outward or on a surface of the inner frame facing towards the lumen (5) respectively in yet other embodiments.

Moreover, the layer (11) of elastic material or the further layer (12) of elastic material can be of a polyurethane fabric such as used in swimming clothes coated with silicone.

Alternatively, the layer (11) of elastic material or the further layer (12) of elastic material can be formed by a polyurethane film deposited onto the braided wire mesh (1000) or inner frame (2) respectively.

In another embodiment the further layer (12) of elastic material does not form a liner for the inner frame from the downstream side (7) to the upstream side (6) completely, but from the downstream side to the leaflets (3) or from the downstream side to between the leaflets and the upstream side (6). In both these embodiments, the fluid flow through the prosthetic heart valve (1) has to pass the lumen and the leaflets (3).

Moreover, the hooks may comprise only one leg or some of the hooks may have two legs and some of the hooks may have one leg.

The inner frame (2) or the braided wire mesh of the flange (4) may be made from other materials suitable for this type of medical use in another embodiment. For instance, the inner frame (2) or the braided wire mesh (4) can be made from another pseudo-elastic metal such as from a Cobalt-Chromium alloy, a Nickel-Cobalt alloy. Alternatively, the inner frame (2) or the braided wire mesh (4) can be made from another material suitable for this type of medical use and deforming reversibly under strains up till 8% or 10%. To be able to deform reversibly under strains up till 8% or 10% between the collapsed condition, the radially uncompressed condition and the target condition means that the inner frame (2) or flange (4) deform without plastic deformation.

The braided wire mesh may be formed out of 2 or more wires in another embodiment.

Alternatively, the wire from which the wire mesh is formed may not have a circular cross section but for instance a square cross section. A circular cross section however is advantageous as frictional forces between the wire sections (20) at the crossings (19). A low friction contributes to the conformability property of the flange (4).

Alternatively, in case the wire (17) has a circular cross section, the wire may have a different wire diameter. Wire (17) with a larger diameter will increase the force needed for the same amount of radial compression which contributes to anchoring. Conformability however improves with a smaller diameter of the wire (17). In addition, wire (17) with a larger diameter is more difficult to process when adding stitches.

In another embodiment the flared portion (9) or the coupling portion (8) comprise a plurality of mazes (100) wherein the first diagonal (21) is smaller than the second diagonal (22) in radially uncompressed condition.

In another embodiment the first dimension (D1) is equal to or smaller than the second dimension (D2) in the radially uncompressed condition.

In another embodiment the layer (11) of elastic material and the further layer (12) of elastic material are partially overlapping to form the seam.

In another embodiment the inner frame (2) does not have a rotationally symmetric circumference around the axis except for where the coupling portion (8) of the flange (4) is connected to the inner frame. By having a rotationally symmetric circumference around the axis where the coupling portion (8) of the flange is connected to the inner frame, the flange (4) is rotationally symmetric at the coupling portion (8) as well. This contributes to the rotationally independent shape and properties of the flange away from the coupling portion (8).

Stents with appropriate dimensions and strength can be used to form the inner frame (2). Therefore, in another embodiment, the inner frame is formed using any of a number of different methods that would be apparent to a person skilled in the art making stents for supporting the leaflets (3), such as etching or water jet cutting. Alternatively, the inner frame (2) is produced by connecting two or more tubular sections together to form a singular tubular inner frame. In case 2 sections are connected, a first inner frame section forms an upstream section and a second inner frame section forms a downstream section.

In another embodiment the prosthetic heart valve (1) is suitable for transcatheter tricuspid valve replacement. In this embodiment the layer (11) of elastic material and the further layer (12) of elastic material are not permeable for blood below a blood pressure of at least 15 mm Hg.

In another embodiment the prosthetic heart valve (1) is suitable for trans-atrial or transapical delivery.

In another embodiment, instead of two leaflets (3) there may be at least one leaflet (3).

In another embodiment the prosthetic heart valve (1) comprises at least one leaflet (3) of another material than bovine pericardium, such as porcine pericardium or a synthetic material. In fact, the at least one leaflet and the further layer (12) of elastic material may be formed from a single sheet of material.

FIG. 7 discloses a prosthetic heart valve structure where the inner frame, e.g., the stent part, and the mesh are made of the same piece of material. In this embodiment the stent and the mesh are made of one and the same wire, e.g, a nitinol wire, which has been braided to form both the mesh and the inner frame. Having the inner frame made of the same wire as the mesh would imply a less rigid inner frame which would be easier to collapse and put in a crimped condition and arrange in the capsule of the delivery tool. It should be appreciated that in another embodiment of the invention, hooks could be made of one and same piece of material as the inner frame and the mesh and being arranged to the inner frame, e.g., the hooks, the inner frame and the mesh could be made from one and the same piece of wire.

The skilled person will appreciate that it may be advantageous to combine some of the alternative embodiments.

The invention claimed is:

1. A prosthetic heart valve for regulating fluid flow between an upstream side and a downstream side and being deformable between a collapsed condition, a radially uncompressed condition, and a target condition, comprising:
   an inner frame having a tubular shape comprising a lumen, the lumen extending from the upstream side to the downstream side in the radially uncompressed condition;
   at least one leaflet arranged within the lumen and arranged for regulation of the fluid flow; and
   a braided wire mesh arranged outside of the inner frame and connected to the inner frame at a coupling portion of the braided wire mesh, the braided wire mesh further comprising a flared portion and a body portion between the coupling portion and the flared portion, wherein in the radially uncompressed condition the flared portion is positioned closer to the upstream side than the coupling portion and the body portion,
   wherein in the radially uncompressed condition the prosthetic heart valve forms a cavity surrounded by the braided wire mesh and the inner frame, the cavity having an opening on the upstream side,
   wherein in the target condition only a part of the length of the body portion along an axis is radially compressed, the axis extending from the upstream side to the downstream side,
   wherein the collapsed condition corresponds to a condition in which the inner frame and the braided wire mesh are radially collapsed over their entire length in axial direction,
   wherein the braided wire mesh has a first dimension along the axis,
   wherein the inner frame has a second dimension along the axis,
   wherein the second dimension is at least as large as the first dimension in the radially uncompressed condition, and
   wherein the first dimension is larger than the second dimension in the target condition under influence of elongation of the body portion of the braided wire mesh under radial compression of the part of the body portion.

2. A prosthetic heart valve according to claim 1, wherein in the radially uncompressed condition the inner frame is rotationally symmetric around the axis at least at the coupling portion.

3. A prosthetic heart valve according to claim 1, wherein inner frame comprises a lumen wall arranged to restrict the flow of blood through the lumen wall.

4. A prosthetic heart valve according to claim 3, wherein the lumen wall comprises a layer of elastic material.

5. A prosthetic heart valve according to claim 4, wherein the braided wire mesh comprises a braided wire mesh surface that at the body portion faces the inner frame, the braided wire mesh surface being lined a liner with low permeability for blood configured to restrict blood flow through the mazes; and wherein the inner frame comprises an inner frame surface facing the cavity, the inner frame surface facing the cavity being lined with the further layer of elastic material formed by a further liner with low permeability for blood.

6. A prosthetic heart valve according to claim 1, wherein the braided wire mesh forms a plurality of mazes each comprising four corners,
   the mazes each have a first diagonal and a second diagonal,
   in the radially uncompressed condition the first diagonal has a larger perpendicular projection in a plane comprising the axis than in a plane perpendicular to the axis, and the second diagonal has a larger perpendicular projection in a plane perpendicular to the axis than in a plane comprising the axis and
   the first diagonal has a smaller dimension than a second dimension in the body portion in the radially uncompressed condition.

7. A prosthetic heart valve according to claim 1, further comprising a layer of elastic material attached to the braided wire mesh to restrict blood flow through mazes of the braided wire mesh.

8. A prosthetic heart valve for regulating fluid flow between an upstream side and a downstream side and being deformable between a collapsed condition, a radially uncompressed condition, and a target condition, comprising:
   an inner frame having a tubular shape comprising a lumen, the lumen extending from the upstream side to the downstream side in the radially uncompressed condition;
   at least one leaflet arranged within the lumen and arranged for regulation of the fluid flow; and
   a braided wire mesh arranged outside of the inner frame and connected to the inner frame at a coupling portion of the braided wire mesh, the braided wire mesh further comprising a flared portion and a body portion between the coupling portion and the flared portion, wherein in the radially uncompressed condition the flared portion is positioned closer to the upstream side than the coupling portion and the body portion,
   wherein in the radially uncompressed condition the prosthetic heart valve forms a cavity surrounded by the braided wire mesh and the inner frame, the cavity having an opening on the upstream side,
   wherein in the target condition only a part of the length of the body portion along an axis is radially compressed, the axis extending from the upstream side to the downstream side,
   wherein the collapsed condition corresponds to a condition in which the inner frame and the braided wire mesh are radially collapsed over their entire length in axial direction,
   wherein
      the braided wire mesh forms a plurality of mazes each comprising four corners and four edges,
      at least three corners form a corner of more than one maze,
      the at least three corners are formed by crossings of a plurality of wire sections, and
      the wire sections are arranged to slide with respect to each other at the crossings.

9. A prosthetic heart valve according to claim 1, wherein the braided wire mesh is formed by a single continuous wire.

10. A prosthetic heart valve according to claim 1, wherein the prosthetic heart valve is arranged for transcatheter delivery.

11. A prosthetic heart valve according to claim 10, wherein the prosthetic heart valve is a prosthetic mitral valve and is arranged for transseptal delivery in a transcatheter mitral valve procedure.

12. A prosthetic heart valve according to claim 1, wherein the wire mesh and the inner frame are made from one and the same piece of material.

13. A prosthetic heart valve for regulating fluid flow between an upstream side and a downstream side and being deformable between a collapsed condition, a radially uncompressed condition, and a target condition, comprising:
- an inner frame having a tubular shape comprising a lumen, the lumen extending from the upstream side to the downstream side in the radially uncompressed condition;
- at least one leaflet arranged within the lumen and arranged for regulation of the fluid flow;
- an outer frame arranged outside of the inner frame and connected to the inner frame at a coupling portion of the outer frame, the outer frame further comprising a flared portion and a body portion between the coupling portion and the flared portion, wherein in the radially uncompressed condition the flared portion is positioned closer to the upstream side than the coupling portion and the body portion, and
- a plurality of hooks attached on the downstream side of the inner frame, each of the plurality of hooks comprising an attachment end attached to the inner frame, a hook body in the uncompressed condition curving from a downstream direction outwardly and in an upstream direction to a top, the top flaring outwardly from the hook body in the radially uncompressed condition, wherein the plurality of hooks are arranged to capture native leaflets in the target condition, the plurality of hooks being distributed at rotationally symmetric positions around the axis,
- wherein in the radially uncompressed condition the prosthetic heart valve forms a cavity surrounded by the outer frame and the inner frame, the cavity having an opening on the upstream side,
- wherein in the target condition only a part of the length of the body portion along an axis is radially compressed, the axis extending from the upstream side to the downstream side,
- wherein the collapsed condition corresponds to a condition in which the inner frame and the outer frame are radially collapsed over their entire length in axial direction.

14. A prosthetic heart valve according to claim 13, wherein the hook body comprises at least one leg having a center line extending between the attachment end and the top and wherein a dimension of the at least one leg perpendicular to the center line tapers at the top.

15. A prosthetic heart valve according to claim 13, wherein the hook body comprises at least one leg and having a center line extending between the attachment end and the top and a dimension of the at least one leg perpendicular to the center line tapers at the attachment end.

16. A prosthetic heart valve according to claim 13, wherein the outer frame, the inner frame and the hooks are made from one and the same piece of material.

17. A prosthetic heart valve according to claim 13, wherein each hook comprises a first leg having a first attachment end attached to the inner frame and a second leg having a second attachment end attached to the inner frame, and wherein the top of the hook couples a second end of the first leg to a second end of the second leg.

18. The prosthetic valve according to claim 17, wherein the first attachment end is attached to the inner frame at a first location and the second attachment end is attached to the inner frame at a second location spaced from the first location.

19. The prosthetic valve according to claim 18, wherein the first location is a first bottom corner of a first maze of the inner frame and the second location is a second bottom corner of a second maze of the inner frame.

* * * * *